United States Patent [19]
DeBusk

[11] Patent Number: 5,575,781
[45] Date of Patent: Nov. 19, 1996

[54] ABSORBENT ARTICLE USEFUL IN MEDICAL APPLICATIONS

[75] Inventor: Autry O. V. DeBusk, Powell, Tenn.

[73] Assignee: DeRoyal Industries, Inc., Powell, Tenn.

[21] Appl. No.: 539,677

[22] Filed: Oct. 5, 1995

[51] Int. Cl.⁶ .................................................. A61F 13/00
[52] U.S. Cl. ............................................ 604/362; 156/204
[58] Field of Search .................................. 604/358, 362, 604/385.1; 602/41, 42, 43; 128/849, 851, 855; 2/275

[56] References Cited

U.S. PATENT DOCUMENTS

| | | | |
|---|---|---|---|
| 422,271 | 2/1890 | West | 2/275 |
| 764,134 | 7/1904 | Laskey | 2/275 |
| 2,493,492 | 1/1950 | Malamut | 604/394 |
| 3,097,649 | 7/1963 | Gray | 604/362 |
| 3,301,257 | 1/1967 | Crowe, Jr. et al. | 128/296 |
| 3,422,816 | 1/1969 | Robinson et al. | 604/362 |
| 3,698,393 | 10/1972 | Stone | 604/362 |
| 3,756,241 | 9/1973 | Patience | 604/362 |
| 3,867,935 | 2/1975 | Eisdorfer et al. | 604/385.1 |
| 4,044,769 | 8/1977 | Papajohn | 604/396 |
| 4,068,666 | 1/1978 | Shiff | 128/290 W |
| 4,205,680 | 6/1980 | Marshall | 604/362 |
| 4,626,251 | 12/1986 | Shen | 604/362 |
| 4,639,253 | 1/1987 | Dyer et al. | 604/362 |
| 5,041,103 | 8/1991 | Rupinskas | |

*Primary Examiner*—David H. Willse
*Assistant Examiner*—Ki Yong O
*Attorney, Agent, or Firm*—Paul E. Hodges, P.C.

[57] ABSTRACT

An absorbent article useful in medical applications and particularly useful as a medical sponge. The article includes a multilayered absorbent web material having at least first and second side edges thereof twice-folded inwardly of the body of the article and at least an elongated radiopaque element anchored and fully covered by the marginal folds of the web material. In one embodiment, there is included a flexible loop element having its opposite ends anchored in the marginal folds of the web material and having the bight portion thereof extending unsupported from its anchoring marginal folds. A method for the manufacture of the absorbent article is disclosed.

14 Claims, 3 Drawing Sheets

5,575,781

ABSORBENT ARTICLE USEFUL IN MEDICAL APPLICATIONS

FIELD OF INVENTION

This invention relates to absorbent articles which are useful in medical applications, and particularly to medical sponges, and more particularly to medical sponges of the laparotomy sponge type.

BACKGROUND OF INVENTION

Surgical sponges, particularly laparotomy sponges, are used extensively in medical procedures, from use as wipe cloths to saline-soaked packing for internal organs which are temporarily stored outside the body cavity during a surgical procedure. Literally millions of these sponges are used annually in the medical industry so that their cost is a very important consideration when examining the overall cost of medical care.

At the time of the manufacture of a medical sponge it is unknown where the sponge may be used, hence it is the common practice in the industry to include in the construction of the sponge at least one radiopaque element that is useful in identification of the sponge when viewed by X-ray. Placement of and adequate anchoring of this radiopaque element to or within the sponge has been problematical in the prior art. To the knowledge of the present inventor, except for those radiopaque elements which have been woven into the material of which the sponge is made or which have been heat-sealed to a sponge, only manual operations have been available to attach the radiopaque element to the sponge. Further, in the prior art sponges where a loop member is provided as a part of the sponge, the ends of the loop being anchored to the sponge at one edge or corner thereof as by stitching, the anchoring of the loop has heretofore been difficult to achieve. Among other desirable or required properties of absorbent articles intended for use in medical procedures, it is required that the article not exhibit cut yarn ends externally of the article where the ends could contact and irritate the patient's tissue, such as when using the article to clean an open wound or to absorb blood or other body fluids from an open body cavity during a surgical procedure. Further, loose yarns or pieces of yarns are not acceptable inasmuch as these act as foreign bodies when present internally of a patient, often resulting in granulomas or initiating other adverse effects.

U.S. Pat. No. 4,068,666 discloses a surgical sponge and method for forming the sponge in which multiple rectangular outer layers of absorbent material, e.g. cotton gauze and a special absorbent inner layer, are overlaid with their side edges in register. An elongated flat strip of radiopaque elastomeric element is laid on the top of the stack with one end of the strip aligned with the side edges of the absorbent material layers and the remainder of the strip projected inwardly of the stack, away from the side edges. This composite is next sewn along the side edges thereof, leaving a portion of the side edges unsewn. This sewing operation captures only one end of the radiopaque element in the stitching so that the remainder of the element is "loose" and can lose its flat profile during use and render the element difficult or even impossible to locate upon X-ray examination of the sponge. Further, the loose end of this element is subject to protrusion through the outer layer of gauze and presenting a highly objectionable source of possible tissue irritation or damage when the sponge is in use.

The sewn composite is then turned inside out, as one turns a bag inside out, through the opening developed by the unsewn portion of the side edges of the composite. This causes all raw edges of the composite layers to be turned inwardly of the composite, except for the unsewn portion of the side edges. This unsewn portion of the side edges is thereupon manually turned inwardly and sewn closed. In one embodiment, the ends of a flat fabric strip, in loop form, are positioned in the unsewn opening before it is sewn closed with the intent of anchoring such ends within the opening as it is sewn closed. The product of this patent has not been successfully marketed, primarily because the fabric loop is inadequately anchored to the sponge and breaks away when in use, and because of the very prohibitive cost of manufacturing the sponge which is occasioned by the large amount of manual labor required in its manufacture. Further, the corners of the loose end of the flat strip of radiopaque material, being in large part loose within the sponge, tended to project through the gauze material which formed to outer layer of the sponge and become a source of irritation to a patient when the corner digs into the patient's body tissue during use of the sponge. Also, as noted above, the loose element is subject to movement that may cause it to become difficult to locate using X-rays. The design and construction of this sponge precludes its manufacture using automatic mechanical means.

It is therefore an object of the present invention to provide a novel absorbent article, particularly a medical sponge.

It is another object of the present invention to provide a medical sponge which includes at least one radiopaque element and which is amenable to manufacture by automatic mechanical means.

It is another object of the present invention to provide a method for the manufacture of an absorbent article which includes a radiopaque element.

It is another object of the present invention to provide an improved laparotomy sponge having at least one radiopaque element securely anchored thereto.

These and other objects and advantages of the invention will be recognized by one skilled in the art given the present disclosure including the drawings in which:

SUMMARY OF INVENTION

Figure 2:
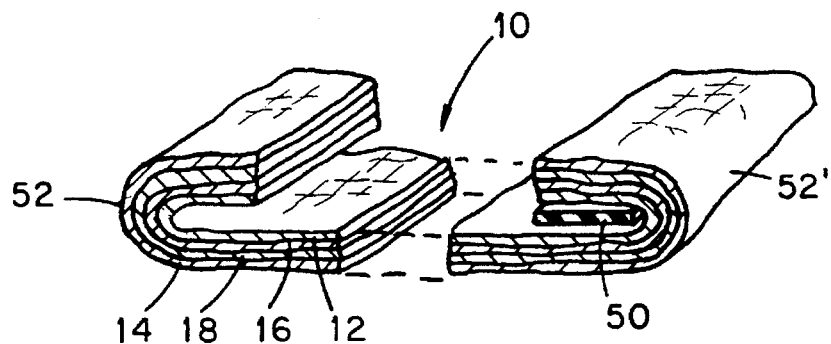
FIG. 2 is a fragmentary and perspective view, taken generally along line 2—2 of FIG. 1, of a portion of the sponge depicted in FIG. 1, but showing only once-folded side edges of the sponge.

In accordance with the present invention there is provided an absorbent article, typified by a laparotomy sponge useful in medical procedures, comprising at least first and second outer substantially rectangular layers of an absorbent material such as woven cotton gauze to form the body of the absorbent article. Each layer includes first and second opposite side edges which have no material loose or cut (raw) yarn ends. Each layer further includes third and fourth opposite side edges which may include cut yarn ends. These several layers are stacked one upon another with the side edges of the several layers in substantial register. The third and fourth side edges (all layers) are folded inwardly twice and the folds so formed are secured in place, as by stitching. Importantly, prior to the inward folding of these sides edges, an elongated flat strip of radiopaque element is overlaid on one of the outer surfaces of the absorbent material, this element being aligned with its longitudinal dimension generally parallel with the side edge with which it is associated. This element is carried inwardly of the absorbent article as its associated side edge is folded inwardly, both during the first fold and during the second fold such that the element is fully captured and buried within the folded side edges of the several layers of the absorbent article. In this position, the whole of the element is covered with multiple layers of the absorbent article and in its buried position, the element is substantially anchored mechanically, and preferably, by the means used to secure the folds in position, e.g. by the stitching used to secure the folds.

In accordance with one aspect of the invention, there is provided a loop member associated with one of the folded side edges of the absorbent article. In this embodiment, in the manufacture of the absorbent article, the ends of the loop member are overlaid on the surface of an outer layer of the absorbent article and within the region of one of the side edges thereof which is to be folded. These ends terminate near the unfolded side edges such that the ends are themselves folded inwardly of the article as their associated side edge is folded inwardly. By this means, the ends of the loop member are twice folded inwardly with the folding of the side edge and thereby mechanically captured and anchored within the folded side edge. The ends preferably are further anchored to the absorbent article by reason of their being bound in the folds by the means used to secure the folds in position, e.g. by stitching used to secure the folds in position. In one embodiment, this loop member comprises a braided strand. Preferably this strand includes a length of filamentary elastomeric radiopaque material captured in the hollow central lumen of the braided strand, thereby imparting radiopacity to the loop member. If desired, the loop member may be in the form of a flat ribbon of folded cloth material, with or without a radiopaque material incorporated therewith. In the present invention, the anchored ends of the loop member remain anchored within the multiple folds of the side edge of the absorbent article even though the stitches give way.

DETAILED DESCRIPTION OF INVENTION

Figure 1:
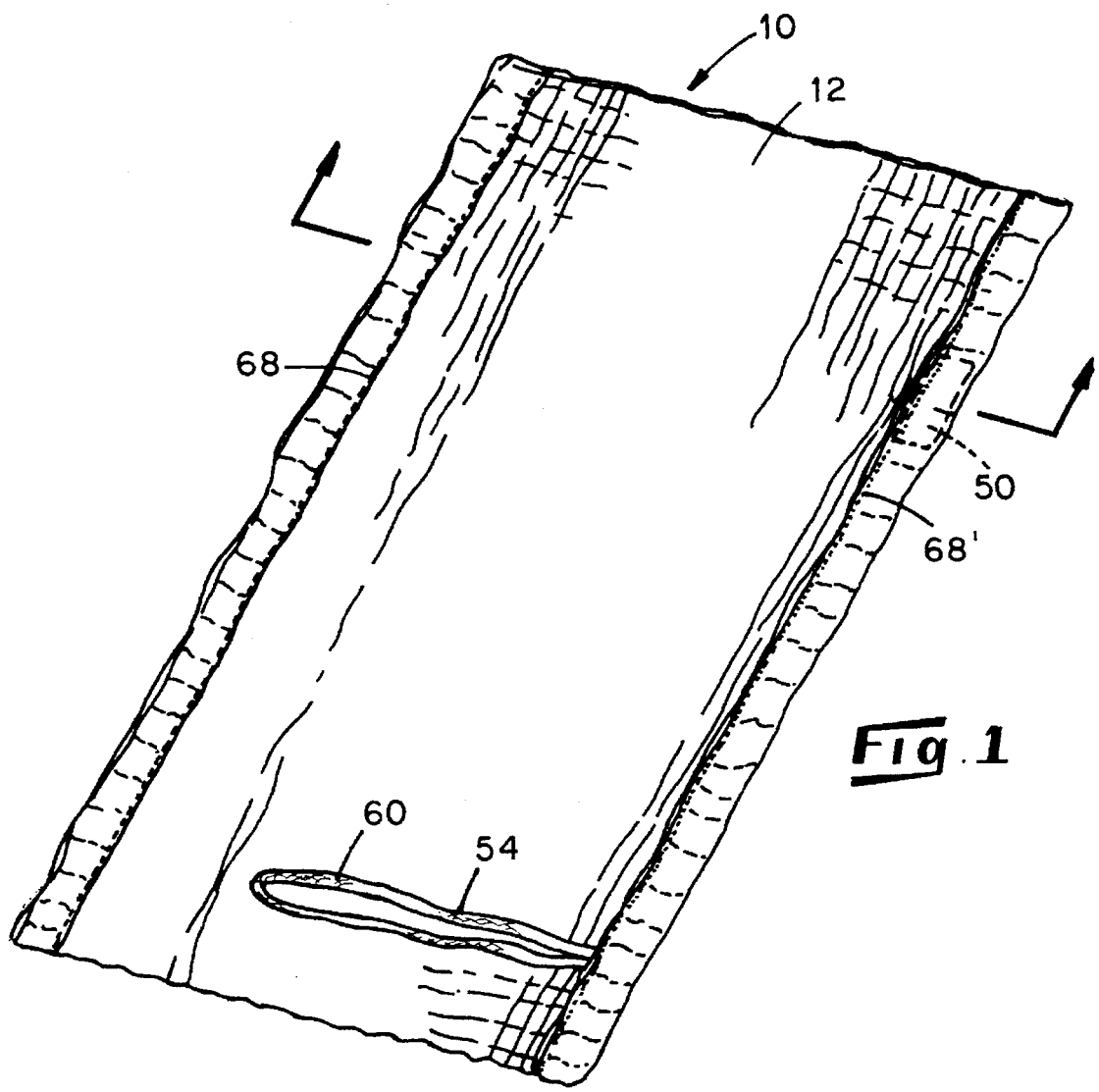
FIG. 1 is a perspective representation of one embodiment of an absorbent laparotomy sponge embodying various of the features of the present invention.
Figure 3:
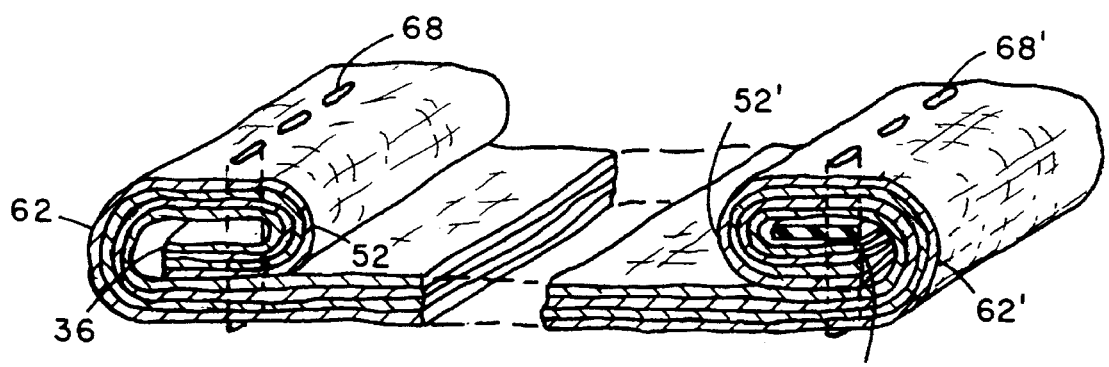
FIG. 3 is a further fragmentary and perspective view, taken generally along line 2—2 of FIG. 1, of a portion of the sponge depicted in FIG. 1, and showing twice-folded side edges of the sponge.
Figure 4:
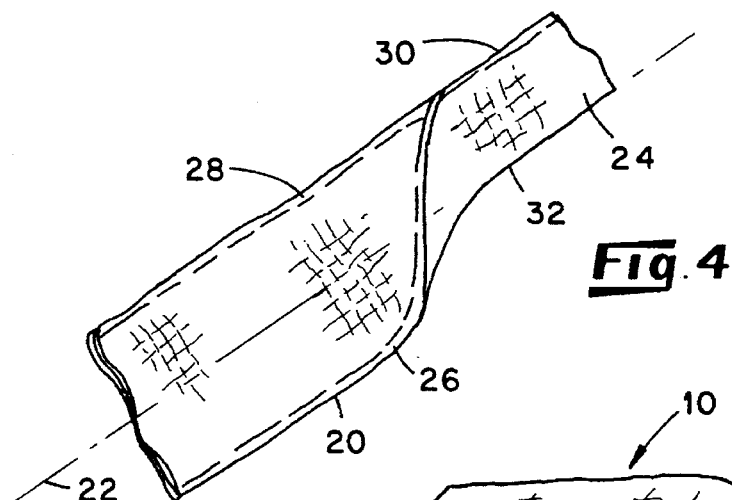
FIG. 4 is a representation of the folding of a two-layered gauze web to form a four-layered gauze web.

With reference to the several Figures, and specifically FIGS. 1–3, the absorbent article 10 of the present invention includes at least a first outer layer 12 of an absorbent material and a second outer layer 14 of absorbent material. In the depicted embodiment, these layers 12 and 14 are rectangular in geometry. As desired, the absorbent article may include one or more additional layers 16 and 18 of absorbent material that are disposed between the first and second outer layers. Most commonly, the first and second outer layers are of a woven gauze material, such as gauze woven from absorbent natural, manmade, or combinations of natural and manmade fibers or filaments. One commonly used material is woven cotton gauze having a thread count of 24×20. Other suitable absorbent materials for use in absorbent articles are well known in the art. The choice of the number of layers of absorbent material to be employed in a given absorbent article is largely determined by the desired absorptive capacity of the article. As desired, a core material of absorbent material such as that sold by Kendall Company, Wellesley Hills, Mass. under its NOVONETTE trademark, may be employed. Referring to FIG. 4, in the present invention, it is preferred to use at least a two-ply gauze web 20 which is of a width that is twice the desired final width of the absorbent article, this two-ply web being folded along its longitudinal centerline 22 to form a four-ply web 24 in which the selvedge edges 26 and 28 of the web are in register and all lie along the same side edge 30 of the four-ply web. By this means, the side edge of the folded web opposite the selvedge edges comprises a fold which has no cut ends of yarns. As desired, stitching or other bonding 29 and 29'(see FIG. 7) may be employed along the side edges 30 and 32 of the fully folded web 20 to preclude separation of the multiple layers of the web and impart integrity to the web. As will appear more fully hereinafter, this four-ply web may serve as the starting material in the present method for manufacture of an absorbent article.

In the manufacture of a typical laparotomy sponge,the web 20 is cut into individual lengths, the cut being made normal to the centerline 22 of the web. A typical cut length of the multilayered web for use in the manufacture of a laparotomy sponge, for example, will measure about 24 inches wide by 24 inches long when laid out flat and before being advanced through the manufacturing apparatus. One suitable flat strip of radiopaque material is that available from AeroQuip of Fitzgerald, Georgia. This material is about ½ inch wide and about 1/64 inch thick. In a laparotomy sponge, for example, a length of about two inches of this material is chosen to make up the desired radiopaque element. Other widths, thicknesses and/or lengths may be employed as desired for a particular absorbent article.

A preferred loop material comprises a length of cord which is braided from polyester yarns and has a central lumen. Preferably the cord has an outer diameter of not greater than about ⅛ inch, but smaller or larger diameters may be employed. Also preferably, the lumen of the braided cord contains therein a length of filamentary elastomeric radiopaque material which extends fully between the opposite ends of the length of cord. One acceptable 0.025 gauge filamentary elastomeric radiopaque material is that available from Quality Profile Services of Council Grove, Kans. The tightness of the braid of the cord is chosen to ensure that no portion of the radiopaque filament protrudes or projects outside the cord.

Figure 5:
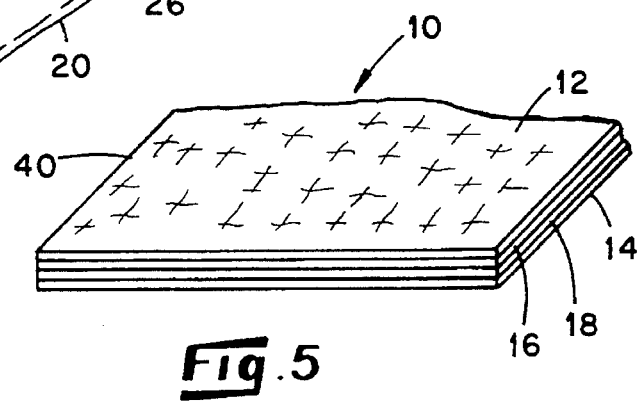
FIG. 5 is a representation of an individual stack of web layers as cut from the web of FIG. 4 and prior to the inward folding of the side edges thereof.

Contrary to the prior art, the absorbent article of the present invention may be manufactured using automated equipment. In accordance with the method of the present invention, a layered web 20 of absorbent material, e.g. cotton gauze, is cut into individual lengths. In one example, the width of the layered web is 24 inches and this layered web is cut into 24-inch lengths (see FIGS. 5 and 7). As noted above, in the preferred web, two opposite side edges 30 and 32 of the layered web comprise either a fold (having no cut yarn ends) or aligned selvedge edges (which also have no cut yarn ends). The cut for dividing this layered web into individual lengths is made normal to the selvedge edges. Therefore, the cut ends of each individual length of web comprise the other two opposite side edges 34 and 36 of the body 38 of the absorbent article. Because of the cut, these edges display raw cut yarn ends. Further, when cut, each individual length comprises a stack 40 of web layers 12–18 which make up the body portion 38 of the absorbent article product.

In the present method, each of the individual lengths of cut layered web (i.e. stack of web layers) is fed forwardly to an apparatus which includes a first set of folders that includes a first folder 44 and a second folder 46. These first and second folders are the leading folders of the apparatus, and are disposed in spaced apart relationship to one another by a distance substantially equal to the width dimension of an individual length of layered web minus twice the width dimension of the first fold to be formed along each of the side edges 34 and 36 of the layered web. At a location in advance of the first set of folders and at a short distance, e.g. about four inches, from the leading end 48 of the layered web as it enters the manufacturing apparatus, a length of elongated flat strip of radiopaque material 50 is overlaid onto the top surface 52 of the top layer 12 of the body portion of the stack of web layers. This strip of radiopaque material is oriented with its length dimension substantially parallel to its associated side edge 34 and with the strip 50 being spaced inwardly of the side edge 34 a distance not greater than about the width of the first fold 52 (see FIGS. 2,3 and 7), and preferably with the outermost side edge of the strip being in substantial register with the side edge 34 of the stack. In this position, the strip of radiopaque material is captured and moved forwardly concurrently with the stack of web layers through the first folder 44 whereupon the first side edge 34 of the stack, with the strip of radiopaque material, is folded inwardly of the body portion 38 such that the strip 50 is captured internally of this first fold 52 (see Figure 2).

Figure 6:
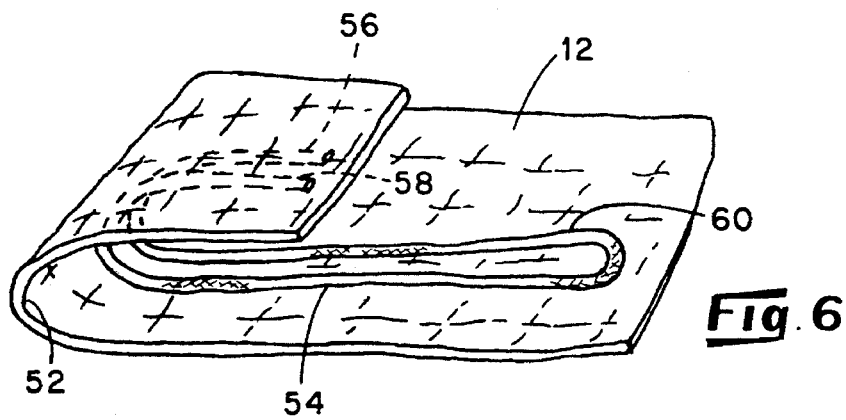
FIG. 6 is a schematic representation, in perspective, of a portion of a single web layer and depicting the placement of the ends of a loop member within one of the side edge folds thereof and prior to the side edge being inwardly folded a second time.

The stack of web layers is further moved forwardly into the manufacturing apparatus and at a location spaced in advance of the trailing end 53 of the stack of web layers, (e.g. about one or two inches in advance of the trailing end of the stack, a loop member 54 is overlaid on the outer surface of the top outer layer 12 of the stack of web layers with the two ends 56 and 58 (See FIG. 6) of the loop member being disposed adjacent one of the side edges of the body portion of the absorbent article. In the depicted embodiment, this loop member 54 is disposed adjacent the side edge 34, but it could be disposed 35 adjacent the side edge 36 if desired. The bight portion 60 of the loop member is allowed to lay loose upon the outer surface of the body portion of the stack. In this position, as the layered web is moved further forwardly into and through the manufacturing apparatus and with its first side edge 34 passing through the first folder 44, the ends of the loop member pass through the first folder concurrently with the side edge 34 of the stack of web layers such that the ends of the loop member are folded inwardly of the body portion along with the first inward fold 52 of the side edge 34 of the stack 40. This same side edge of the stack which has been first folded inwardly of the body portion of the stack, and having the strip of radiopaque material and the ends of the loop member captured within the first fold, is fed through a second folder 46. Thereupon the side edge 34 and its captured components are folded inwardly of the body portion of the stack a second time. This action causes the entire area of the strip of radiopaque material and the ends of the loop member to be also further folded inwardly with the formation of the second fold 62 and to cause these components to be further mechanically anchored in their respective positions along the length of and within the twice-folded side edge 34 of the body portion of the absorbent article product.

As the stack of web layers is fed through the manufacturing apparatus, preferably that side edge 36 of the layered web opposite the side edge 34 which bears the strip of radiopaque material and the loop member passes through the third and fourth folders 64 and 66 and is also folded inwardly of the body portion of the stack in substantially the same manner as the side edge 34.

In a further step in the manufacture of the present absorbent article, the twice-folded side edges of the web are anchored to the body portion of the stack of web layers as by stitching 68 and 68' (See FIG. 3) along the length of the folded side edges 34 and 36. To this end, stitching units 69 and 70 re provided downstream of the third and fourth folders. In the course of this stitching operation, the threads of the stitching are caused to pass fully through the strip of radiopaque element 50 and through the ends of the loop member 54 to further anchor these components within the folds, hence within the absorbent article product. Notably, the full length of the strip of radiopaque element 50 is engaged by the stitching thereby ensuring that this element retains its flat profile during use so that the element can be readily detected by X-ray examination of the absorbent article. Further, the full area of the radiopaque element and the ends of the loop member are strongly mechanically anchored within the folds of their respective side edge of the absorbent article.

Figure 7:
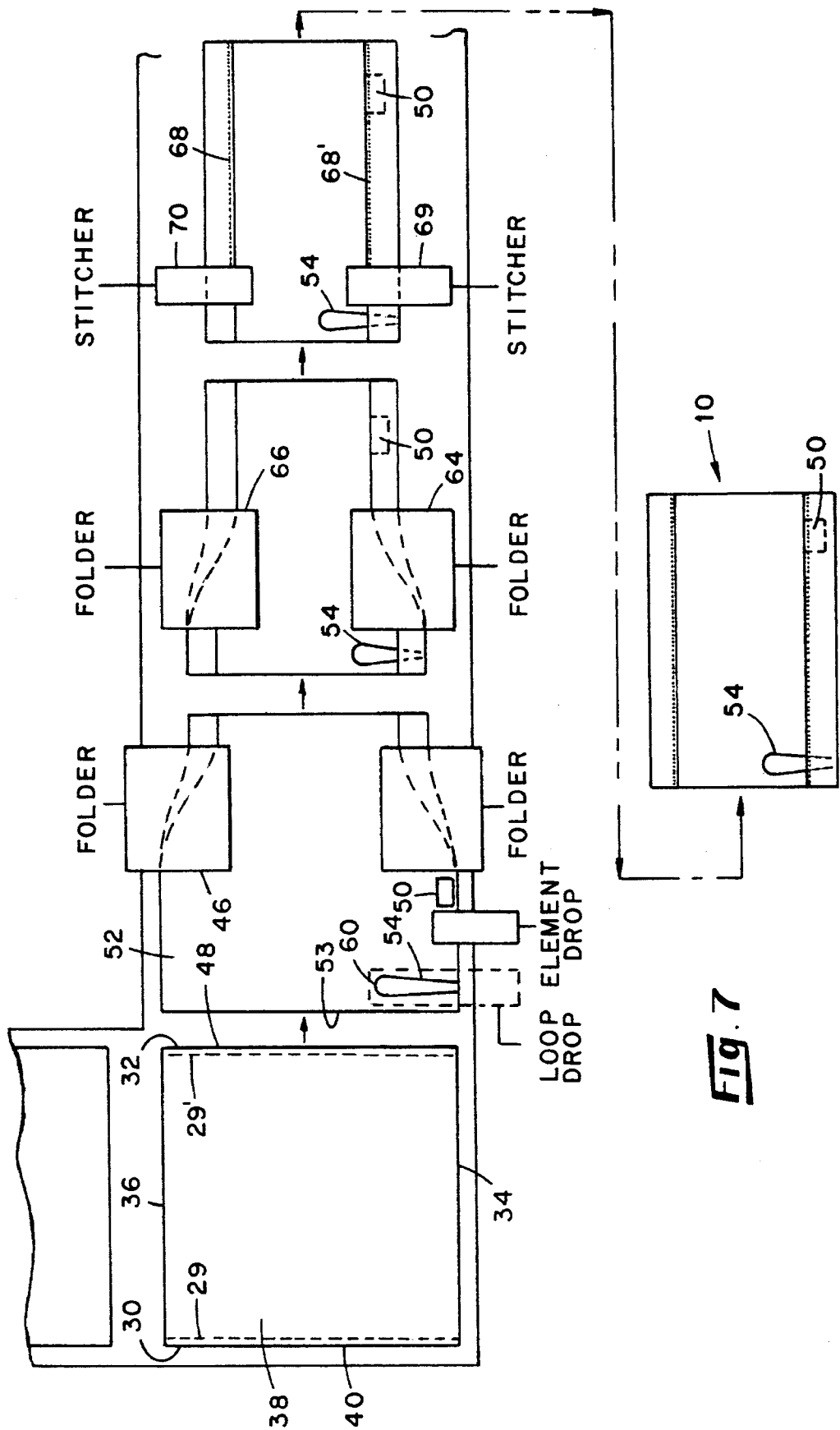
FIG. 7 is a schematic representation of the steps of the method of the present invention and apparatus for carrying out the method.

Referring to FIGS. 4 and 7, in a preferred embodiment of the method of the present invention, a running length of a two-ply web 20 of absorbent material, such as cotton gauze, is folded along its centerline 22 to form a four-layered web 24 in which the selvedge edges 26 and 28 of the web are substantially in register. This web is then cut into individual lengths, the cut being made normal to the length dimension of the web, to form a four-layered stack 40 of web layers. This cut develops cut yarn ends along two of the opposite side edges 34 and 36 of the layers of the stack, the other two opposite side edges 30 and 32 of the layers being selvedge edges (along one of these other side edges) and a fold (the fold line along which the two-layered web was folded to form the four-layered web).

Each individual stack of web layers is then fed forwardly into an apparatus which includes means, such as moving belts, for conveying the stack of web layers into and through the apparatus. Adjacent the input end of the apparatus there are provided first and second folders, one on each of the opposite sides of the apparatus and the two folders being spaced apart by a distance approximately equal to the width dimension of a stack of web layers minus the combined width of the two folds which are formed by these folders.

As the stack of web layers is fed forwardly, a length of flat ribbon of a radiopaque material 50 is overlaid on the upper surface of the top layer of the stack at a location adjacent one of the side edges 34 of the stack. This ribbon is oriented with its length dimension substantially parallel to its associated side edge and, preferably sufficiently near the side edge as to cause the ribbon to be folded inwardly with the web layers as the stack and the overlaid ribbon are fed forwardly through the first folder 64.

Following overlayment of the ribbon of radiopaque material onto the stack of web layers, the stack and ribbon are concurrently fed forwardly into and through the first folder whereupon the side edges of the layers of the stack, and the ribbon, are folded inwardly of the body of the absorbent article a single fold to cause the side edges, and the ribbon, to overlie the body of the stack. By this means, the ribbon is captured between four upper and four lower layers of the stack, these layers fully covering the entire area of the ribbon. Preferably, this initial fold is captured between a pair of conveyor belts (not shown), one engaging the upper surface of the stack and one engaging the bottom surface of the stack, to temporarily hold the fold in place as the stack is fed further into the apparatus toward third and fourth folders.

When it is desired that the absorbent article include a loop member, as the stack of web layers is being fed forwardly into the apparatus, and at a location ahead of the first folder and downstream of the trailing end of the stack of web layers, there is deposited onto the upper surface of the top layer of the stack of web layers a loop member. As described hereinabove, the loop member includes two ends that are positioned close together and a bight portion. The two ends are positioned near the side edge 34 of the stack such that these ends are folded inwardly of the body of the stack as the side edges of the layers of the stack and the ends of the loop member are fed forwardly into and through the first and second folders. By this means, the ends of the loop member fold over upon themselves, and most commonly tend to spread laterally to become aligned more with the length dimension of the fold rather than normal to the length dimension of the fold. This causes the ends to be more likely to be engaged by the means used to secure the fold in position against the body of the stack as will be noted hereinafter.

The stack of web layers with the length of radiopaque material, and the loop when such is used, is thereafter fed forwardly through the apparatus whereupon the length of radiopaque material and the first fold pass into and through the third folder to form a second fold of the side edges of the layers inwardly of the body of the absorbent article. This second fold causes the ribbon to be covered with an additional four layers of web material on the bottom of the ribbon, thereby ensuring that no portion of the ribbon, especially its corners, will project out of the layers to engage and irritate a patient. Further, this second fold enhances the mechanical capture of the ribbon within the folds.

The forward movement of the stack of web layers through the apparatus carries the side edges of the stack and the accompanying length of radiopaque material and the loop member into and through the folders.

As the stack of web layers is fed forwardly through the apparatus, the first and second folds on each of the opposite side edges of the stack are passed through stitchers where the folds are anchored in position with respect to the body portion of the stack as by means of stitching. In a preferred embodiment, this stitching passes through the thickness of the radiopaque ribbon and all layers of the stack and further anchors the ribbon in place within the folds. Further forward movement of the stack of web layers through the apparatus carries the entire length of each side edge through its respective stitcher. As the loop member passes through a stitcher, the stitches also engage the ends of the loop member that are disposed within the folds of the side edge 34 to become more securely anchored to the body portion of the absorbent article product.

It will be noted that only those side edges of the stack of web layers which include cut yarn ends need be passed through the folding and stitching operations. The other opposite side edges of the layers in the stack comprise either a fold or a selvedge edge, hence no cut yarn ends, and therefore need not be folded and stitched.

In some applications, the folded and stitched stack of web layers, which is now a useful integrated absorbent article, may be treated as by washing to remove natural oils, etc. from the yarns, and/or to soften the webs and/or to impart bulk to the article.

Whereas the present invention has been described in certain specific terms, it is to be recognized that it is intended to limit the invention only as set forth in the appended claims.

What is claimed:

1. An absorbent article particularly suitable for use in medical applications comprising a body portion including a plurality of layers of an absorbent material, said layers being overlaid one on the other in stacked relationship to define a stack of said layers, said layers within said stack having first and second opposite side edges, at least one elongated relatively flat radiopaque element having a length dimension associated with at least one of said first and second side edges, said radiopaque element being disposed adjacent said at least one of said first and second side edges and oriented with its length dimension generally parallel to said at least one of said first and second side edges, said at least one of said first and second side edges being first folded inwardly of said body portion with said radiopaque element being simultaneously folded inwardly of said body portion with the inward folding of said at least one of said first and second side edges to define a first fold having a width dimension that includes the radiopaque element, and thereafter further folded inwardly of said body portion to define a second fold within which the first fold and said radiopaque element associated therewith are captured therein, whereby said radiopaque element is substantially fully disposed in said first and second folds and physically anchored therein by said folds.

2. The absorbent article of claim 1 and including a loop member having opposite first and second ends and a bight portion, said first and second ends being overlaid on said body portion adjacent one of said first and second side edges and with the ends being disposed substantially flush with said one of said first and second side edges, whereby said loop ends are first folded inwardly of said body portion simultaneously with the inward folding of said at least one of said first and second side edges to define said first fold that includes the loop ends, and thereafter further folded inwardly of said body portion to define a second fold within which the first fold and the loop ends associated therewith are captured therein, with said bight portion of said loop being unsecured to said absorbent article.

3. The absorbent article of claim 1 or 2 and including means securing said first and second folds in their folded condition.

4. The absorbent article of claim 1 wherein said body portion thereof includes at least four layers of absorbent gauze.

5. The absorbent article of claim 4 wherein said at least four layers are established by folding a single layer of absorbent gauze upon itself first and second times.

6. The absorbent article of claim 5 wherein said single layer of absorbent gauze includes first and second opposite selvedge side edges and, when folded upon itself a first time, said selvedge side edges overlie one another.

7. The absorbent article of claim 6 wherein said at least one of said first and second side edges with which said at least one radiopaque element is associated is a side edge other than said first and second opposite selvedge side edges.

8. The absorbent article of claim 1 wherein said width dimension of said first inward fold is approximately one-half inch.

9. The absorbent article of claim 2 wherein said loop member includes a central lumen and a length of radiopaque material disposed within said lumen.

10. The absorbent article of claim 2 wherein said at least one radiopaque element and said loop member are associated with, one of said first and second side edges.

11. A method for the manufacture of an absorbent article comprising the steps of assembling a stack of web layers of an absorbent material including a top layer having a top surface and first and second opposite side edges, thereafter disposing an elongated radiopaque element having a length dimension on said top surface of said top layer of said stack, said element being oriented with its length dimension substantially parallel to one of said first and second opposite side edges of said stack, thereafter feeding said stack of absorbent material, with said radiopaque element disposed thereon, forwardly through a first folding location wherein at least one side edge of said stack is folded inwardly of said stack to form a first fold with said radiopaque element captured internally of said fold and fully covered by said web layers of said stack, thereafter feeding said stack of absorbent material through a second folding location wherein at least said one side edge of said stack is further folded inwardly of said stack to form a second fold which contains said first fold and the radiopaque element associated therewith.

12. The method of claim 11 and including disposing a loop member on said top surface of said top layer of said stack, said loop member including a cord or flat ribbon having opposite ends and a bight portion, the ends of said loop member being disposed adjacent to and oriented substantially normal to one of said first and second opposite side edges of said stack, and thereafter feeding said stack with said loop member disposed thereon through a further folding location wherein said loop ends are first folded inwardly of said body portion simultaneously with the inward folding of said at least one of said first and second opposite side edges to define a first fold that includes the loop ends in first fold and thereafter feeding said stack of absorbent material through a still further folding location wherein at least said one side edge of said stack is further folded inwardly of said stack to capture a said first fold and the ends of said loop member associated therewith in said second, said bight portion of said loop being unsecured to said absorbent article.

13. The method of claim 11 or 12 and including securing said first and second folds in their folded positions relative to said stack.

14. The method of claim 11 wherein assembling of said stack of web layers includes the step of providing a web of absorbent material having opposite selvedge side edges and folding said web along its longitudinal centerline to overlay said opposite selvedge side edges one on the other and in substantial register.

* * * * *

UNITED STATES PATENT AND TRADEMARK OFFICE
CERTIFICATE OF CORRECTION

PATENT NO. : 5,575,781
DATED : November 19, 1996
INVENTOR(S) : Autry O. V. DeBusk It is certified that error appears in the above-indentified patent and that said Letters Patent is hereby corrected as shown below:

Column 5, line 52, delete "35".

Column 8, line 53, delete "a" and substitute --said-- therefor.

Column 9, line 15, delete the comma , and substitute --a common-- therefor.

Column 10, line 16, delete "define a first fold that includes" and substitute --capture-- therefor.

Column 10, line 16, delete "first folds" and substitute --said first fold-- therefor.

Column 10, line 20, delete "a".

Column 10, line 21, following "second" and preceding the comma , insert --fold--.

Signed and Sealed this

Twenty-second Day of July, 1997

*Attest:*

BRUCE LEHMAN

*Attesting Officer*     *Commissioner of Patents and Trademarks*